United States Patent [19]

Graham

[11] Patent Number: 4,508,625

[45] Date of Patent: Apr. 2, 1985

[54] MAGNETIC SEPARATION USING CHELATED MAGNETIC IONS

[76] Inventor: Marshall D. Graham, 6 Temple St., Framingham, Mass.

[21] Appl. No.: 539,542

[22] Filed: Oct. 6, 1983

Related U.S. Application Data

[63] Continuation-in-part of Ser. No. 435,015, Oct. 18, 1982, abandoned.

[51] Int. Cl.³ ............................................... B03C 1/00
[52] U.S. Cl. .................... 210/695; 210/927; 435/2; 435/34; 435/173; 435/261
[58] Field of Search ............... 210/695, 651, 222, 223, 210/927; 424/101; 435/173, 253, 261, 29, 294, 2, 34; 436/63, 174, 177, 526

[56] References Cited

U.S. PATENT DOCUMENTS

| | | | |
|---|---|---|---|
| 3,375,925 | 4/1968 | Carpenter | 210/222 X |
| 3,700,555 | 10/1972 | Widmark et al. | 435/29 X |
| 3,709,791 | 1/1973 | Lichtenstein | 435/294 |
| 4,047,814 | 9/1977 | Westcott | 356/38 |
| 4,116,829 | 9/1978 | Clark et al. | 210/222 X |
| 4,187,170 | 2/1980 | Westcott et al. | 210/222 X |

OTHER PUBLICATIONS

Owen, J. Appl. Phys., 53(5), May 1982, pp. 3884–3887.
Evans et al., Science, vol. 213, Aug. 7, 1981, pp. 653–654.
Nassimbeni et al., Acta Cryst., (1979), B35, pp. 1341–1345.
Andres, J. S. African Institute of Mining Tech., vol. 76, Oct., (1977), pp. 113–116.
Andres, Materials Sci. & Eng., 26, (1976), pp. 269–275.
Evans et al., J. Biochem. Biophys. Methods, vol. 2, pp. 11–18, (1980).
Roy et al., Clin. Chem., vol. 26, No. 13, pp. 1919–1920, (1980).
Melville et al., IEEE Transactions on Magnetics, vol. Mag 11, No. 6, Nov., (1975), pp. 1701–1704.
Graham, J. Appl. Phys., vol. 52(3), Mar. 1981, pp. 2578–2580.

Primary Examiner—Richard V. Fisher
Assistant Examiner—W. Gary Jones
Attorney, Agent, or Firm—Lahive & Cockfield

[57] ABSTRACT

Disclosed is a new method for magnetic separation from a carrier fluid of biological cells or other organic or inorganic particles having a negative surface charge. A paramagnetic salt is mixed with an aqueous solution of a chelating agent, for example EDTA. The cells or particles to be separated are mixed with this paramagnetic carrier solution, and the resulting mixture is exposed to a high gradient magnetic field. The cells or particles attract the chelated paramagnetic cations preferentially to the carrier solution such that the particles develop a magnetic susceptibility greater than that of the carrier liquid. The method achieves highly repeatable separations at lower magnetization fields than existing high gradient magnetic separation methods. Feasibility has been shown for erbium chloride and dysprosium chloride, with whole blood as the sample. In this instance, single-pass magnetic separation efficiencies significantly greater than those attainable with paramagnetic erythrocytic hemoglobin are readily available.

34 Claims, 1 Drawing Figure

MAGNETIC SEPARATION USING CHELATED MAGNETIC IONS

REFERENCE TO RELATED APPLICATIONS

This application is a continuation-in-part of copending U.S. application Ser. No. 435,015 entitled, "Magnetic Separation of Biological Cells and Other Small Particles from Carrier Fluids Employing Lanthanide Chelates", filed Oct. 18, 1982, now abandoned.

BACKGROUND OF THE INVENTION

The invention relates to the separation by magnetic means of biological cells and other small particles from a carrier. Particularly, this invention relates to the magnetic separation of such cells or particles having very low levels of intrinsic paramagnetic or diamagnetic susceptibility, but which have in aqueous suspension a net negative surface charge. Examples of particles meeting these conditions include blood formed bodies, epithelial cells (whether isolated or clusters of individual cells), almost all other animal and bacterial cells, and many viruses. Examples of other small particles include organic material such as tissue fragments, and also inorganic material such as sand, sediments of iron oxide, and the like. The particle size of inorganic material can vary from 0.1 to 10 microns or more.

The use of magnetic techniques for separating diamagnetic white blood cells and certain other mammalian cells from a carrier is known. These techniques require that the cells either phagocytose magnetic particles or be bound to some particle sufficiently magnetic to permit external magnetic fields to remove the cells with their internalized or bound magnetic particles. These methods suffer from at least two disadvantages. An incubation period is necessary to permit phagocytosis or binding to occur, during which the cells may incur damage. Also, the unphagocytosed or unbound particles may remain free in the processed sample, or may be freed as a result of further sample processing, so that analysis by cytometric techniques such as COULTER volume analysis is complicated or impossible. Furthermore, such analysis as is possible may be affected adversely by the cellular degradation resulting from the incubation required to allow the cells to interact with the magnetic particles. These previous methods, however, do permit use of magnetic-field strengths available from laboratory magnets to achieve the actual cell separation from the carrier.

The use of magnetic techniques for separating red blood cells from a carrier is also known in the art. This separation relies on induction of a paramagnetic state in the intracellular hemoglobin of such cells. Several species of hemoglobin or hemoglobin derivatives are paramagnetic, of which high-spin ferrous deoxyhemoglobin or ferric methemoglobin are the most important biologically. The former hemoglobin species can be induced by treating red cells with a carrier containing 10 mM sodium dithionite in physiological saline, and the latter by similarly treating the red cells with 20 mM sodium nitrite. See M. D. Graham, J. Appl. Phys. Vol. 52 (3), pages 2578-80, 1981.

While such methods permit useful separations of red cells, they require use of relatively harsh, non-physiologic chemicals which may adversely affect later use of cells for some application where either the white cells in the filtrate or the retained red cells may need to be metabolically normal. In addition, the separation itself requires products of magnetic intensities and gradients that restrict these hemoglobin conversion techniques to use with large and expensive magnetic circuits including permanent magnets, superconducting solenoids, or laboratory electromagnets to provide the necessary high gradient magnetic (HGM) fields. Further, packing of the filter used to remove the paramagnetic cells must be carefully controlled, or the cells will pass through the filter without coming within interaction range of its magnetized matrix due to the weakness of the magnetic forces acting on the red cells. Finally, low carrier flow rates must be used or the viscous fluid forces will overpower the weak magnetic forces and carry the cells through the filter. Practically, carrier flow rates must be kept at levels sufficiently low that samples cannot be processed quickly enough for efficient analysis by automated cell counters, for example.

FIG. 1 in the cited publication shows the field-dependency of magnetic separation efficiency for red blood cells suspended in carrier containing 10 mM dithionite or 20 mM nitrite. At field strengths of 1.0 Tesla and carrier flows of 1.0 ml/minute, filtration times of more than one minute were required to achieve cell separations of approximately 70%. This separation efficiency is too low, and the filtration times are too high, for use with modern instruments. Separations exceeding 85% efficiency were obtained at field intensities of 2.0 Tesla, but were unacceptably variable from sample to sample. In addition, field intensities above 0.8 Tesla are very difficult to obtain in a filter system small enough for practical laboratory use. If carrier flow rates were increased to reduce the filtration time, magnetic separation efficiency would further decrease, or even more intense magnetic fields would have to be used. Thus, when paramagnetism is induced in the red cells through use of carriers capable of converting intracellular hemoglobin into paramagnetic species, basic technical problems limit the separation levels achievable with field strengths available from permanent magnets or small electromagnets.

The other blood formed bodies, the platelets, are not known to be magnetically separable by either of the two mechanisms just discussed. Of other cell types, certain cells not normally found in the peripheral blood are known to phagocytose particles, a characteristic which has been used to separate them from mixtures of cells by adding magnetic particles to the cellular suspension and incubating it, as has been described. Remaining mammalian cells, including epithelial cells, have not been demonstrated to be magnetically separable by any mechanism. Bacterial cells are known to be magnetically separable by trapping them in a flocculating agent containing magnetic particles and applying known magnetic filtration methods to separate the flocculent masses.

Westcott et al., in U.S. Pat. No. 4,047,814, U.S. Pat. No. 4,187,170, and J. Biochemical and Biophysical Methods, Vol. 2, pages 11-18 (1980) describe two methods for the magnetic separation of a material of interest from a background substance.

In one method, a material (including bacteria) which is "essentially non-magnetic and thus by itself not sufficiently responsive to the magnetic field to separate from the background substance" is combined with a magnetizing solution containing the salt of a magnetic element. The atoms of the magnetic element are said to attach to the available sites on the molecules of the non-magnetic material so as to develop in that material a magnetic susceptibility. When the composite sample is passed through a magnetic field the material is transported to a region where it can be analyzed and recovered. The process specifically names ferric chloride, manganese chloride, erbium chloride, dysprosium chloride, terbium chloride, and holmium chloride as useful salts of magnetic atoms.

In the second method, a material which has low positive or negative magnetic susceptibility, and which does not form attachments readily (or at all) with magnetic atoms, as in the case of starch, is separated by suspending it in a magnetic salt solution which when subjected to the attraction of a magnetic field develops a differential attractive force. The fluid itself has a positive magnetic susceptibility so that it is attracted toward the magnetic field, producing a pressure (or density) gradient and pushing the particles away from the magnet. In this instance the magnet attracts the fluid, and the nonmagnetic or weakly magnetic particles to be separated are forced away from the magnetic field. The net force on the particles is proportional to the difference in susceptibility of the fluid and the particles. For this process only ferric chloride and manganese chloride are claimed.

Neither of the foregoing methods are stated to be useful for the separation of animal cells, nor for separation of red blood cells (erthrocytes). Indeed, since divalent and trivalent ions such as those formed when the salts disclosed by Westcott et al. are dissolved in water are well-known to cause clumping of cells through a bridging mechanism, it is unlikely that isolated cells can be separated by the methods described. In addition, salts such as taught by Westcott et al. tend to produce, when dissolved in water, a low solution pH incompatible with cellular integrity. Further, several of the salts, particularly those of the lanthanide metals, have low levels of solubility in water, and precipitate out in solutions of physiologic pH, or when many common buffers are used to restore solution pH to such levels.

Lanthanide ions have been widely used as calcium analogs in studies characterizing transport processes in membranes, an application in which they show high-affinity binding. Binding of lanthanides for use as a fluorescent or nuclear magnetic resonance probe is also known. The calcium analog and membrane probe studies have been done on membranes derived from cells, not on intact cells. Consequently there was no concern for cellular integrity in this prior art, nor was bridging between membranes necessarily detrimental. However, in applications of magnetic separation methods to biological cells, both maintenance of cellular integrity and freedom from cellular clumping are crucial.

Paramagnetic carrier fluids, including those taught by Westcott et al, have been considered for at least two decades as magnetically controlled density media for separation of inorganic, diamagnetic, and weakly paramagnetic materials. More recently, use of such carriers in HGM systems for separation of minerals and non-ferrous metal particles and oxides has been investigated. Because of their paramagnetic moments, lanthanides have been considered for magnetogravimetric systems such as described in the second method of Westcott et al. while manganese chloride has been used in HGM separation work. These efforts depend on the particles being less paramagnetic than the carrier fluid, i.e., relatively diamagnetic.

SUMMARY OF THE INVENTION

It has now been discovered that chelates of paramagnetic metal ions are attracted to particles having negatively charged surfaces, particularly biological surfaces such as cell surfaces, and impart to the particles a magnetic susceptibility which is significantly greater than the magnetic susceptibility of the carrier fluid. More specifically, it has been discovered that the addition to such particle suspensions of chelated paramagnetic ions results in a significant increase in the difference between the magnetic susceptibility of the particles and the background fluid relative to prior art techniques. Accordingly, effective magnetic separations are possible with less powerful magnetic fields or at higher flow rates. The use of chelating agents in such systems permits one to choose from a wider variety of paramagnetic ions, increases the effective solubility of the paramagnetic metal ions, and decreases the sensitivity of the separation process to solution pH. Perhaps most important, the use of chelated paramagnetic metal ions can remove completely the tendency of cells in blood samples (or other animal cells) to clump on exposure to multivalent metal ions.

Thus, in its broadest aspects the process of the invention enables the separation of particles having a negative surface charge from a carrier liquid and comprises the steps of contacting the particles with a chelated paramagnetic metal ion to develop a magnetic susceptibility associated with the particles greater than the magnetic susceptibility of the carrier liquid, and then applying a magnetic field to the particles and carrier liquid to separate a portion of the particles from the liquid.

In preferred embodiments, the paramagnetic ion, such as dysprosium, erbium, holmium, terbium, thulium, gadolinium, iron, cobalt, manganese, or mixtures thereof, is chelated with a polyamino polycarboxylic acid chelating agent such as ethylenediaminetetraacetic acid (EDTA). Other useful chelating agents include diethylenetriamine-pentaacetic acid (DTPA), triethylenetetraaminehexaacetic acid (TTHA), N-hydroxyethylenediaminehexaacetic-acid (HEDHA), ethyleneglycolbis(betaaminoethyl ether)-N,N'-tetraacetic acid (EGTA), 1,4,7-triazacyclononane-N,N',N"-triacetic acid (NOTA), 1,4,7,10-tetraazacyclododecane-N,N',N",N"'-tetraacetic acid (DOTA), and N'hydroxyethylenediamine-N,N,N'-triacetic acid (HEDTA). The currently perferred paramagnetic metal ions are the paramagnetic lanthanides, most preferably erbium and dysprosium. The currently preferred chelate is EDTA. Lanthanides belong to the family of rare-earth metals, which are expensive. By forming a chelate compound of the lanthanide, the amount of rare-earth metal required for a given level of binding is reduced, so that the process becomes more cost effective.

One method of conducting the separations involves passing the carrier liquid with suspended particles and adsorbed metal chelate through a matrix, e.g., a filter element of ferromagnetic material, disposed within a magnetic field to retain a substantial portion of the particles within the matrix. The particles subsequently may be collected by flushing the matrix with a chelate-free solution, a solution containing a different chelate, a solution containing the same chelate at a different concentration from the originally employed concentration, or a solution containing a substance, e.g., metal ions or certain dyes, which competes with and displace the paramagnetic metal ions associated with the particles.

Another method of practicing the invention involves passing a liquid column comprising suspended particles and carrier fluid through one or more magnetic fields, or repeatedly through the same field, so that the velocity of the particles is altered preferentially to the velocity of the carrier liquid. In one method of practicing this embodiment of the invention, the particles and carrier liquid are forced through a conduit, typically having an inside diameter in the 20–500 micrometer range, which directs the flow of particles through the field, plural fields, or repeatedly through the same field. This may result in chromatography-like process which produces plural fractions rich in particles substantially homogeneous with respect to their affinity for the paramagnetic metal chelate.

The approach of this invention accordingly depends on the particles to be separated developing a net paramagnetism relative to the carrier fluid due to concentration of the paramagnetic metal chelate on the surface of the particles. This net paramagnetism permits separation of the particles using HGM filtration or related magnetic separation methods, but because its magnitude is a function of the concentration of paramagnetic metal chelate in the carrier fluid, useful separations can be achieved at higher carrier flow rates, and therefore shorter filtration times or at lower magnetic field intensities as compared with existing separation methods. Specifically, small HGM filtration systems incorporating permanent magnets as the field source are feasible using the methods of this invention. As an illustration, 1″ by 1″ samarium-cobalt magnets one-fourth inch in thickness have been used with a ferritic filter matrix to provide separation efficiencies of 97% for 35 mM dysprosium chelates from a high gradient magnetic filtration system occupying less than one cubic inch.

This method permits magnetic separation of cells from whole blood, with repeatabilities and efficiencies heretofore unattainable. The superior magnetic separation efficiencies permit practical separations at lower fields than is possible with existing methods, and the new process need not visibly affect cellular integrity. Using this invention, single-pass magnetic separation efficiencies significantly greater than those attainable with paramagnetic erythrocytic hemoglobin are possible e.g., 90% versus 37%, at 0.3 Tesla and 0.75 ml/min flow rate. The method requires no lengthy cellular incubations and is not technically demanding. There is no interference with cell counting due to unbound or dislodged chelated paramagnetic metal ion. Packing of the matrix into the filter was found to be much less critical than with previous separation methods due to the strong interaction between the cells with bound paramagnetic metal chelate and the matrix material.

According to the process of the invention, biological cells or other small particles having a net negative surface charge when in suspensions are magnetically separated from their carrier fluid. In the case of blood samples, the sample may be diluted, e.g., with isotonic saline, and a solution of a paramagnetic metal ion chelate may be added to the dilute cell suspension. Alternatively, the chelate may be formed in situ in the prediluted sample, or the sample may be diluted in a single step with a pre-formed solution of known concentration of chelated paramagnetic metal ion. The paramagnetic metal ion chelate immediately becomes associated with the cells or other negatively charged particles thereby developing in the particles a magnetic susceptibility greater than the magnetic susceptibility of the carrier liquid. When a magnetic field is applied to such suspensions, the particles are preferentially affected by the field, and the phenomenon can be exploited to conduct effective magnetic separations.

The separations can be conducted using a filter, preferably including ferritic material, or by forming the suspension into a liquid column which is passed through one or more fields one or more times. Examples of particles which may be separated include blood formed bodies, epithelial cells (whether isolated or clusters of individual cells), and almost all other animal and bacterial cells and virus particles. Examples of other small particles include organic material such as cell organelles or tissue fragments, and inorganic material such as sand, sediments of iron oxides, and the like.

BRIEF DESCRIPTION OF TABLE AND DRAWING

Experimental data for filtration of human blood cells are reported in Table I, using EDTA chelated erbium (chloride salt) and in FIG. 1 using both erbium and dysprosium chelate.

DESCRIPTION OF THE PREFERRED EMBODIMENTS

Figure 1:
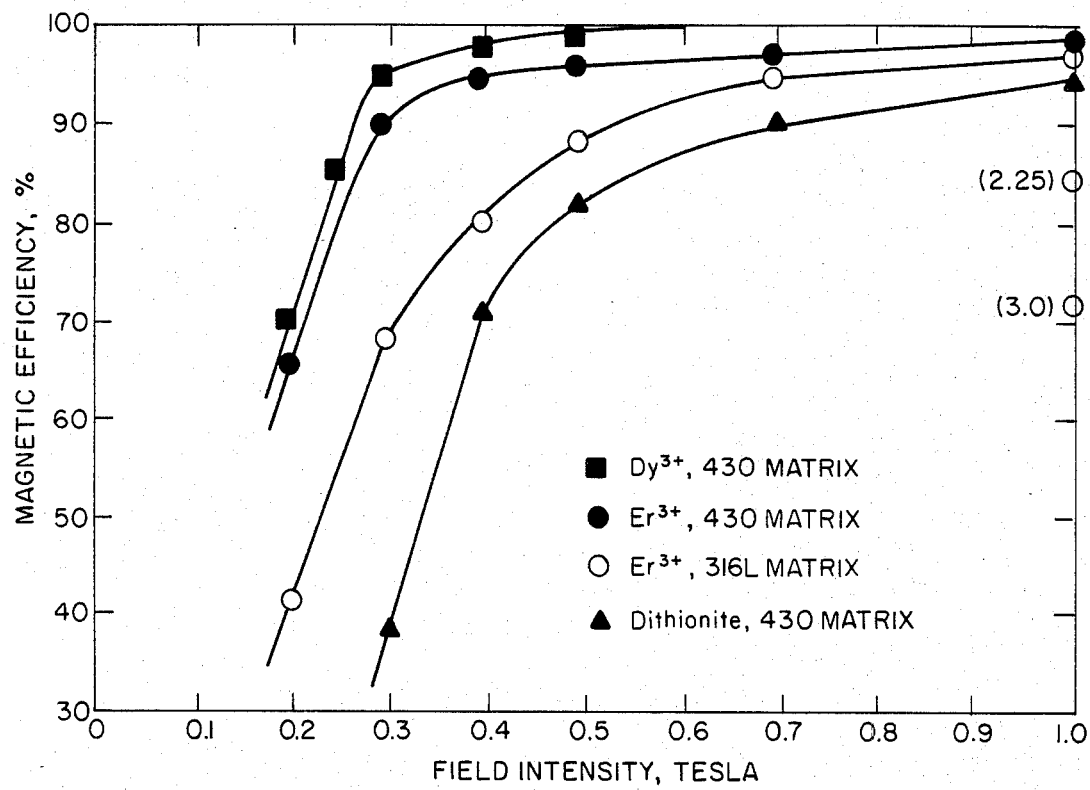

Venous blood samples were drawn from volunteers into evacuated tubes (6451 Vacutainer; Becton-Dickinson) containing 10.5 mg disodium EDTA. The samples were verified for normalcy (COULTER COUNTER Model S-Plus; Coulter Electronics, Inc.) before use on the day of drawing. Manual 1:101 dilutions were made in polystyrene flasks and shaken gently to give homogeneous cell suspensions.

Separability of cells from carrier fluids was examined using a High-Gradient Magnetic Separation (HGMS) system. The filter was a D-shaped plastic chamber 13 mm long and 118 mm$^2$ in cross-section, filled with stainless steel wire as noted. Packing was random, but with the major component parallel to flow. The filter was mounted between 50 mm polepieces on a 10 cm electromagnet (V-4005, with a V2901 supply; Varian Associates) and subjected to magnetizing fields up to 2 Tesla (T) as measured with a Hall effect guassmeter (615, with HTBl-0608 probe; F. W. Bell, Inc.). Suspension flows upward through the filter were controlled by a variable-speed syringe pump, fitted with a 3 ml syringe to contain the cell suspension.

Unless otherwise noted, to clean the matrix and to clear the circuit of air, the filter was flushed manually with 15 ml of the experimental carrier solution before each separation determination. With the electromagnet still de-energized, the circuit was then overfilled rapidly with the corresponding cell suspension, and the syringe pump was activated. After 1.2 ml of cell suspension had been delivered at the chosen flow rate, a one-milliliter aliquot (A1) of filter effluent was collected for use in calculating mechanical filtration levels. With filter backflow prevented, the pump syringe was refilled, the magnet energized at the preselected field intensity, and the delivery and collection (aliquot A2) steps repeated. This sequence was repeated for each selected combination of flow rate and field intensity. A 2 ml control aliquot (A3) was taken for each suspension from the reservoir used to fill the filter and the syringe pump. The aliquots were analyzed for cell count and volume, count data (A1, A2, A3) being used to calculate filter characteristics as follows (for percentages, multiply by 100:)

Mechanical Filtration, $F=(A3-A1)/A3$
Magnetic filtration, $M=(A1-A2)/A3$
Magnetic efficiency, $E=(A1-A2)/A1=M/(1-F)$
Total Filtration, $T=(A3-A2)/A3=M+F$ In Table I, the filtration data at 0.75 ml/min is reported for whole blood diluted 1:101 with the working solution including erbium chelate at the indicated concentration. The matrix material was unannealed, 316L austenitic stainless wire, 35 micrometers in diameter, randomly packed to 11.4% of the filter volume. Table I summarizes experimental filtration data according to the concentration of $Er(EDTA)^-$ in the carrier solution, and includes for comparative purposes, sodium dithionite at 10 mM final concentration as a substitute for the chelated lanthanide. The solution osmolarity was adjusted to that of 40 mM erbium chloride by addition of sodium chloride. In a second experiment, 10 mM sodium dithionite in isotonic saline buffered with phosphate was employed. For both, deoxygenation was confirmed spectrophotometrically. Data for various field intensities are given for the higher chelate concentrations, all at constant flows of 0.75 ml/min. Carrier solutions used in each of the stated concentrations of the lanthanide chelate were prepared as described in Example 1.

TABLE I

| (Er3+) | Field (T) | E (%) | M (%) | F (%) | T (%) |
|---|---|---|---|---|---|
| 1 mM | 2.03 | 31.6 | 24.6 | 22.2 | 46.8 |
| 5 mM | 2.03 | 83.2 | — | — | — |
| 10 mM | 2.03 | 96.6 | 90.8 | 6.0 | 96.8 |
|  | 1.00 | 83.2 | — | — | — |
| 20 mM | 1.00 | 94.2 | — | — | — |
| 40 mM | 1.00 | 94.8 | 93.1 | 1.7 | 94.B |
|  | 0.48 | 92.4 | 86.8 | 6.0 | 92.8 |
|  | 0.28 | 71.7 | 67.4 | 6.0 | 73.4 |
| 50 mM | 1.00 | 98.7 | 92.9 | 5.9 | 98.8 |
|  | 0.48 | 91.1 | 85.7 | 5.9 | 91.6 |
| 50 mM* | 1.00 | 98.4 | 94.1 | 4.3 | 98.4 |
|  | 0.48 | 92.2 | 88.2 | 4.3 | 92.5 |
| 10 mM* | 1.00 | 76.9 | 68.4 | 11.0 | 79.4 |
|  | 0.30 | 13.0 | 11.6 | 11.0 | 22.6 |

*Sodium dithionite, substituted for erbium chloride and EDTA.

At identical HGM conditions, 10 mM erbium chelate gave separations exceeding those for equimolar dithionite, a concentration well above that known to produce complete deoxygenation of cellular hemoglobin. The data demonstrate that the diamagnetic blood cells acquire useful paramagnetic contrast over the paramagnetic carrier solution, giving practical separations at 2 Tesla of cells from whole blood suspensions containing $Er(EDTA)^-$ concentrations in the 5 mM range. Thus, separations were possible at relatively low magnetic fields, of cells from whole blood in a carrier containing centimolar levels of the chelated lanthanides, erbium or dysprosium, chelated with EDTA to form, generically, $Ln(EDTA)^-$.

FIG. 1 shows the field-dependency of separation efficiency for blood cells suspended in 40 mM $Ln(EDTA)^-$, or in 10 mM sodium dithionite, at 0.75 ml/min. The 316L stainless matrix was used to acquire data indicated by open circles, including the comparative flow data at 2.25 and 3.0 ml/min. Other data were acquired with a 430 stainless mesh woven of wire 50 micrometers in diameter, filling 15.5% of the filter.

The tabular data emphasize an important advantage of the technique. Although the cellular magnetic contrast is concentration limited, the operative limit is not the cencentration of an intrinsic cellular component as with the hemoglobin-conversion mechanisms, but rather is the concentration of sites on the cell surface binding the extrinsic chelate. Consequently, magnetic separation efficiencies exceeding those currently available are easily attainable at chelated paramagnetic metal concentrations giving physiologic osmolarities. Further, in the case of particles other than cells, or if the cellular sequelae of elevated osmolarities can be accepted, metal chelate concentrations above 35 mM can be used to realize single pass separation efficiencies not readily obtainable with the conversion mechanisms and permitting use of considerably lower magnetizing fields, as shown by FIG. 1. Higher flow rates can also be used. A flow-dependency study at 1.0 Tesla (see FIG. 1) show separations of 94.8%, 94.3%, 83.5%, and 71.3% at 0.75, 1.5, 2.25 and 3.0 flow in ml/min, respectively, for a concentration of 40 mM $Er(EDTA)^-$.

Erythrocyte suspensions in 40 mM erbium and dysprosium chelate solution exhibit a relative cellular magnetic susceptibility (magnetic contrast) of $25.9 \times 10^{-6}$ MKSu and $34.5 \times 10^{-6}$ MKSu, respectively. These figures are approximately 5 to 7 times greater than the relative paramagnetism attainable with hemoglobin conversion mechanisms which give corresponding contrasts of $5.17 \times 10^{-6}$ MKSu (for deoxyhemoglobin) and $2.81 \times 10^{-6}$ MKSu (for methemoglobin).

Also illustrated in Table I is the consistency observed in separation efficiency. Compare the two sequences for 50 mM erbium chelate concentration. These were completed on consecutive days, using the same batch of carrier solution but blood from different donors. Similarly, identical efficiencies of 94.8% were obtained in the 40 mM, 1.0 Tesla, flow-dependency and concentration-dependency studies, although done on different days using different donors. Note too the consistency below saturation of separation efficiencies at constant products of ion concentration and field intensity, e.g., 5 mM at 2.0 Tesla and 10 mM at 1.0 Tesla; or 10 mM at 2.0 Tesla, 20 mM at 1.0 Tesla and 40 mM at 0.48 Tesla. Separation efficiencies were more repeatable than those reported previously with either sodium dithionite deoxygenation or (particularly) nitrite oxidation (FIG. 2 of cited paper). The metal chelate solutions were also more stable than the sodium dithionite solutions.

Cellular hemoglobin remains in the oxygenated (and therefore the antagonistically diamagnetic) state throughout the separation process. Cell lysis was not detected. Cellular morphology was not visibly altered (beyond reversible osmotic effects), and cell clumping due to the presence of a heavy metal did not occur. The cells were readily removed from the matrix by flushing with isotonic saline (0.9% NaCl by weight containing no metal chelate). Separated cells were mainly erythrocytes due to the thousand-fold superiority in natural occurence, but other blood formed bodies also bind the paramagnetic chelates and so were retained. Specifically, magnetic efficiencies for white cells in buffy-coat concentrates were comparable to those for whole blood, while platelets could be separated from platelet-rich plasma at efficiencies of about 27%.

When the flushing saline contained 50% of the carrier concentration of paramagnetic metal chelate, 62% of the retained cells were removed; when 25% of the carrier metal chelate concentration was used in the flushing saline, 90% of the retained cells were removed. This demonstrates differential fractionation of retained cells according to their binding affinity.

For the 430 ferritic matrix, the pattern seen for the 316L matrix was again obtained, except that the differences favoring erbium chelate were accentuated by the more easily magnetized 430 alloy. With erbium chelate, separations exceeding 90% could be achieved at fields of 0.3 Tesla, at which value only 37% separation was demonstrated for sodium dithionite. At identical flows, sodium dithionite required a field of 0.7 Tesla to provide an efficiency of 90%. At 1.0 Tesla with erbium chelate, single-pass magnetic efficiencies greater than 99% were attained at flows of 0.75 ml/min. Repeatable separations at such efficiencies are not practical with sodium dithionite.

As indicated in FIG. 1, Dy(EDTA)$^-$ consistently gave magnetic separation efficiencies some 5% greater than Er(EDTA)$^-$, below saturation levels. The separation mechanism with both chelated paramagnetic metal ion is clearly superior to the known magnetic separation technique.

The polyamino polycarboxylic acid chelates such as EDTA are strong chelating agent for metal ions, forming stable chelate rings. At a suitable pH, some bind alkaline earth, lanthanide and other metal ions in a largely non-ionic form, but with some monovalent characteristics due to the position of the metal ion in the chelate ring. Thus, such chelates can diminish or effectively eliminate the divalent or trivalent properties of the metal ion and eliminate the tendency for ionic bridging between cell membranes so that cellular clumping does not occur. In addition, the solubility of the metal chelates is greater than the solubility of the free ion at physiological pH, so that greater effective paramagnetic metal ion concentrations can be maintained in solution. The chelate solution is stable in the presence of various buffers so that solution pH can be brought into and maintained in a physiologically acceptable range.

The following, non-limiting examples will further illustrate the invention.

EXAMPLE 1

Erbium chloride was dissolved in water via chelation with EDTA. Carrier solutions of 100 cc each, containing erbium chloride in the concentration of 2 mM, 5 mM, 10 mM, 20 mM, 40 mM and 50 mM respectively and EDTA in a molar ratio of 1.1:1 with the erbium chloride were prepared in the following manner for use in obtaining the data reported in Table I.

Three stock solutions were made using deionized water:

1. 220 mM disodium EDTA (S-311; Fisher Scientific Co.).
2. 200 mM PIPES, 1,4-piperazine bis(ethanesulfonic acid), free acid, (P6757; Sigma Chemical Co.), pH adjusted to 7.1 with sodium hydroxide for use as a buffer.
3. 3M sodium chloride (S-270; Fisher Scientific Co.).

For each molar concentration set forth in Table I, 100 ml of a carrier solution was prepared by removing the required amount of solid erbium chloride hexahydrate (20, 321,-1; Aldrich Chemical Co.) from a desiccator and adding the amount of each of the first two stock solutions required to give a molar ratio of 1.1:1 of the EDTA with the erbium chloride. The volume was then brought to 75 ml with deionized water, and the materials were mixed in a plastic container. The solution pH was adjusted to 7.0 to 7.1 by adding sodium hydroxide solution. The osmolarity was then adjusted to physiological levels of about 300±10 mOs/L, the 100 ml volume being completed with deionized water. Carrier solutions were prepared within two hours of each experiment from stock solutions no more than one week old.

EXAMPLE 2

The above procedures were followed substituting the equivalent amount of dysprosium chloride for the erbium chloride in order to obtain the values reported in FIG. 1.

EXAMPLE 3

In each of the above examples the equivalent amount of the chloride or other salt of other paramagnetic metals, and especially lanthanides such as terbium, holmium, thulium, and gadolinium can be substituted for the erbium chloride, since these salts have high paramagnetic properties.

EXAMPLE 4

8.0 g of $MnCl_2.4H_2O$ were chelated with EDTA as set forth in example 1, and added to diluted whole blood samples such that the concentration of chelated manganese was 40 mM. When this sample was passed upwardly through a filter element of the type described above containing a matrix of 430 stainless wire at a flow rate of 0.75 ml/min, the following separation efficiencies were observed at the following field strengths.

| Field Strength | Efficiency |
| --- | --- |
| 0.3 T | 74.5% |
| 0.4 T | 83.9% |
| 0.5 T | 89.8% |

The cells exhibited some signs of abnormal morphology not seen with the lanthanide chelates despite the identical osmolarity of the carrier solution. This example demonstrates that paramagnetic ions other than lanthanides may be used in the process.

The development of magnetic susceptibility contrast between the cells and background liquid is believed to involve the interaction of the paramagnetic metal ion chelate with negative charge sites on the particle surfaces, through the functional monovalency resulting from the close-range bipolarity of the chelate ring. Once the chelate is bound to a particle there is apparently no tendency for the particle to form another bond with any other particle since the chelate ring's relatively diffuse region of negative charge is directed outward from the binding site, thus repelling other negatively charged particles, or particles to which the lanthanide chelates have bound. The diffuseness of the negative charge region of the chelate ring also makes the ring's binding preferential for negative charge sites. Whatever the reason, no tendency toward clumping of the particles is noted, whether the particles are organic or inorganic.

Most biological materials including cells, tissues, cells derived from tissues, and fragments thereof, and particles of much inorganic material, are known to have negative surface charge in aqueous suspension. Thus, the binding shown by paramagnetic metal chelate is one generally applicable to a wide range of materials, making possible their separation by magnetic means. Further, many intracellular structures are known to have negative binding sites. For a given cellular species, or for a given inorganic particle, binding of the paramagnetic metal chelate is dependent on its concentration in the carrier fluid and on chemical environment.

While the lanthanide chelate normally will not permeate cellular membranes, it can be trapped inside cells by hyperosmotic shock or by treating the cells with permeabilizing agents, as is well known in the cell-loading art. A second separation mechanism is, therefore, possible for biological cells, in which the cells are made to internalize paramagnetic metal chelate prior to magnetic filtration or separation.

Once the particles are separated from the carrier, they may be removed from the filter readily by flushing the filter with a saline solution containing none of the chelate. Alternatively, if it is desired to further fractionate the retained particles according to their binding affinity, for example, it is possible to do so by flushing the filter with a series of solutions containing progressively decreasing amounts of the chelate or of other metallic chelates or by using solutions of various electrolytes such as calcium which compete for the chelating agent.

These methods may be combined with ones in which the paramagnetic metal chelate is internalized by hyperosmotic shock or permeabilizing agents and bound to intracellular structures. By choice of permeabilizing technique it is known to be possible to internalize selectively the carrier fluid into certain cell types, and it has been demonstrated in this work that the retained cells can be fractionated according to binding affinity of the paramagnetic chelate bound to their outer surface. Thus, by choosing combinations of permeabilizing agent prior to filtration and flushing solution to selectively remove retained cells absorbing chelate, distinct fractions can be obtained. Those cells binding chelate only on their surface will be released together if, for example, a flush solution containing no chelate is used. Alternatively, they can be fractionated if desired by controlling the concentration of the chelate in the flushing solution, as has been described. Cells containing internalized chelate can then be removed using well known methods such as high velocity flushing.

Since the paramagnetic metal chelates are soluble and not particles themselves, material bound to particles is not disloged easily by further handling, and unbound material does not cause spurious counts when the retained particles or filtrate are analyzed with cell or particle counters.

In addition to blood cells, epithelial cells and sand particles have been shown to bind sufficient lanthanide chelate as to be attracted to ferritic wires immersed in the same carrier fluid as used for the blood cells and exposed to a magnetic field of 1.0 Tesla. When epithelial cells were suspended in the carrier and the mixture was passed through the same filter as used for blood cells, magnetic separations of more than 83% were obtained for buccal epithelial cells and more than 78% for cervical epithelial cells. These larger cells tended to clog the filter, so results were more variable than for blood cells. Fine sediments from ground building sand could be separated at magnetic separation levels of 32% for fields of 1.0 Tesla, and it is believed that this could be improved by proper filter design. These examples demonstrate the generality of the binding mechanism and illustrate the variety of materials which can be separated by the new method.

The invention may also be practiced by passing a liquid column of the paramagnetic metal chelate-treated particle suspension through one or more magnetic fields one or more times. This results in an alteration of the velocity of the particles in the column relative to the carrier liquid which may be exploited to effect separation of at least a portion of the particles from the liquid. A currently preferred embodiment of this technique involves forcing the suspension through a 20–500 micron I.D. conduit, preferably comprising ferritic material or housing a ferritic wire. The conduit is arranged to direct the column of suspension through one or more fields, which may vary in field strength, or through the same field repetitively. Practice of this technique results in the retardation of the velocity of the particles in the conduit relative to the carrier liquid and consequent separation of a portion of the particles from the liquid carrier. This technique will be further understood from the following example.

EXAMPLE 5

Diluted whole blood treated with paramagnetic metal chelate as set forth in example 1 was passed through a glass capillary having an inside diameter of 120 microns with the aid of gravity and a diaphragm pump at a flow rate of a few microliters/minute. The capillary was looped to form four substantially concentric coils which were placed with one half their circumference between the pole pieces of a laboratory electromagnet. In passing through the conduit, the liquid column passed through the magnetic field gradient eight times. The magnetic field was set at 2.0 Tesla. When no ferritic material was associated with the capillary, a separation efficiency of 18% was observed. When a 50 micron stainless wire was present in the lumen of the capillary, a separation efficiency of 31% was observed. It may be advantageous to periodically interrupt the magnetic field or fields when practicing the invention in this way.

Other embodiments are within the following claims.

What is claimed is:

1. A process for separating particles having a negative surface charge from a carrier liquid, said process comprising the steps of:
    A. contacting said particles with an amount of a chelated paramagnetic metal ion sufficient to develop a magnetic susceptibility associated with the particles greater than the magnetic susceptibility of said carrier liquid; and
    B. applying a magnetic field to said particles and carrier liquid to separate at least a portion of said particles from said carrier liquid.

2. The process of claim 1 wherein said particles comprise organic particles.

3. The process of claim 2 wherein said particles comprise cells.

4. The process of claim 3 wherein, prior to step B, said chelated paramagnetic metal ion is transported into said cells.

5. The process of claim 4 wherein step B is conducted by passing said cells and carrier liquid through a matrix disposed within said magnetic field to retain a substantial portion of said cells within said matrix.

6. The process of claim 5 comprising the additional step of removing a portion of said cells from said matrix by flushing with a member selected from the group consisting of chelate-free solutions, solutions of chelate differing in chelate concentration from the chelate solution resulting from step A, solutions containing a substance which competes with said paramagnetic metal ions for chelation sites, and combinations thereof.

7. The process of claim 1 wherein said paramagnetic metal ion is a lanthanide metal ion.

8. The process of claim 1 wherein said chelated paramagnetic metal ion is chelated with EDTA.

9. The process of claim 1 wherein said chelated paramagnetic metal ion is chelated with a polyamine polycarboxylic acid chelating agent.

10. The process of claim 9 wherein said chelating agent is selected from the group consisting of EDTA, DTPA, TTHA, HEDHA, EGTA, NOTA, DOTA, and HEDTA.

11. The process of claim 1 wherein said paramagnetic metal ion is selected from the group consisting of ions of dysprosium, erbium, holmium, terbium, thulium, gadolinium, iron, manganese, cobalt, and mixtures thereof.

12. The process of claim 1 wherein said paramagnetic metal ion is selected from the group consisting of the ions of dysprosium and erbium.

13. The process of claim 1 wherein step B is conducted by passing said particles and carrier liquid through a matrix disposed within said magnetic field to retain a substantial portion of said particles within said matrix.

14. The process of claim 13 wherein said particles comprise cells, said process comprising the additional step of removing a portion of said cells from said matrix by flushing with a member selected from the group consisting of chelate-free solutions, solutions of chelate differing in chelate concentration from the chelate solution resulting from step A, solutions containing a substance which competes with said paramagnetic metal ions for chelation sites, and combinations thereof.

15. The process of claim 1 wherein step B is conducted by passing a liquid column comprising said particles and said carrier liquid through said magnetic field to alter preferentially the velocity of said particles.

16. The process of claim 15 wherein said column is passed through a plurality of magnetic fields.

17. The process of claim 15 wherein said column is passed through a conduit which directs said liquid column through said magnetic field.

18. The process of claim 17 wherein said conduit comprises ferritic material.

19. The process of claim 17 wherein said conduit surrounds a ferritic wire.

20. The process of claim 17 wherein said conduit is shaped to direct said column repeatedly through said magnetic field.

21. A process for separating cells from an aqueous extracellular fluid, said process comprising the steps of:
A. contacting said cells with an amount of chelated paramagnetic metal ion sufficient to increase the magnetic susceptibility of said cells relative to said extracellular fluid without clumping said cells; and
B. applying a magnetic field to said cells and extracellular fluid to separate a portion of said cells from said extracellular fluid.

22. The process of claim 21 wherein said paramagnetic metal ion is a lanthanide metal ion.

23. The process of claim 21 wherein said chelated paramagnetic metal ion is chelated with EDTA.

24. The process of claim 21 wherein the paramagnetic ion used in step A is chelated with a physiologically compatible chelator and wherein cells separated in step B are substantially undamaged.

25. The process of claim 21 wherein said paramagnetic metal ion is selected from the group consisting of ions of dysprosium, erbium, holmium, terbium, thulium, gadolinium, iron, cobalt, manganese, and mixtures thereof.

26. The process of claim 21 wherein said paramagnetic metal ion is selected from the group consisting of dysprosium and erbium.

27. The process of claim 21 wherein step B is conducted by passing said cells and extracellular fluid through a matrix disposed within said magnetic field to retain a substantial portion of said cells within said matrix.

28. The process of claim 27 comprising the additional step of removing a portion of said cells from said matrix by flushing with a member selected from the group consisting of chelate-free solutions, solutions of chelate differing in chelate concentration from the chelate solution resulting from step A, solutions containing a substance which competes with said paramagnetic metal ions for chelation sites, and combinations thereof.

29. The process of claim 21 wherein step B is conducted by passing a liquid column comprising said cells and said carrier liquid through said magnetic field to alter preferentially the velocity of said cells.

30. The process of claim 29 wherein said column is passed through a plurality of magnetic fields.

31. The process of claim 29 wherein said column is passed through a conduit which directs said liquid column through said magnetic field.

32. The process of claim 31 wherein said conduit comprises ferritic material.

33. The process of claim 31 wherein said conduit surrounds a ferritic wire.

34. The process of claim 31 wherein said conduit is shaped to direct said column repeatedly through said magnetic field.

* * * * *

UNITED STATES PATENT AND TRADEMARK OFFICE
CERTIFICATE OF CORRECTION

PATENT NO. : 4,508,625
DATED : April 2, 1985
INVENTOR(S) : Marshall D. Graham

It is certified that error appears in the above-identified patent and that said Letters Patent are hereby corrected as shown below:

In the last reference of the first column of the title page under Other Publications after "mining" delete "Tech" and insert --and metallurgy--; "1977" should read --1975--.

Column 1, line 66 "application" should read --applications--.

Column 3, line 26 "are" should read --is--; line 58 "diamagnetic, and" should read --diamagnetic or--.

Column 4, line 67 "displace" should read --displaces--.

Column 5, line 33 after "provide" insert --erythrocytic--.

Column 6, line 22 "chelate" should read --chelates--.

Column 6, line 43 "guassmeter" should read --gaussmeter--.

Column 7, line 32 "94.B" should read --94.8--; line 37 "50mM*" should read --50mM--.

Column 9, line 19 after "technique" insert --for erythrocytes--; line 20 "chelates" should read --chelators--; line 21 "agent" should read --agents--;
line 47 after "the" insert --erbium-- and after "Table I" insert --and Fig. 1--; line 60 "20, 321,-1;" should read --20,321,-1;--; line 68 after "mOs/L" insert --with the third stock solution--.

Column 10, line 63 "chelate" should read --chelates--.

UNITED STATES PATENT AND TRADEMARK OFFICE
CERTIFICATE OF CORRECTION

PATENT NO. : 4,508,625

DATED : April 2, 1985

INVENTOR(S) : Marshall D. Graham

It is certified that error appears in the above-identified patent and that said Letters Patent is hereby corrected as shown below:

Column 11, line 44 "disloged" should read --dislodged--.

Signed and Sealed this

Twenty-fifth Day of February 1986

[SEAL]

Attest:

DONALD J. QUIGG

Attesting Officer

Commissioner of Patents and Trademarks